(12) United States Patent
Pauker et al.

(10) Patent No.: US 6,358,199 B1
(45) Date of Patent: *Mar. 19, 2002

(54) DRIVE MEANS FOR FLEXIBLE EVERSION TUBE SYSTEM

(75) Inventors: Fritz Pauker, Wiffertshausen/Friedberg;
Thomas Viebach, Pischertshofen;
Robert Pauker, Kissing; Gerhard Weiglhofer, Schwabhausen/Weil, all of (DE)

(73) Assignee: STM Medizintechnik Starnberg GmbH, Weinheim (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/305,850

(22) Filed: May 5, 1999

(30) Foreign Application Priority Data

May 6, 1998 (DE) ..................................... 298 08 180 U

(51) Int. Cl.[7] ................................................ A61B 1/00
(52) U.S. Cl. ..................... 600/114; 600/102; 600/104; 604/271; 604/172
(58) Field of Search ................................ 600/101, 102, 600/104, 114, 115, 116, 118, 156, 153; 604/95, 96, 271, 172

(56) References Cited

U.S. PATENT DOCUMENTS

| | | | | |
|---|---|---|---|---|
| 4,946,440 A | * | 8/1990 | Hall | 604/95 |
| 5,045,070 A | * | 9/1991 | Grodecki et al. | 604/271 |
| 5,236,423 A | * | 8/1993 | Mix et al. | 604/271 |
| 5,259,364 A | * | 11/1993 | Bob et al. | 128/4 |
| 5,346,498 A | * | 9/1994 | Greelis et al. | 606/108 |
| 5,562,601 A | * | 10/1996 | Takada | 600/114 |
| 5,586,968 A | | 12/1996 | Gründl et al. | |
| 5,882,294 A | * | 3/1999 | Storz et al. | 600/114 |
| 6,071,234 A | * | 6/2000 | Takada | 600/114 |
| 6,077,219 A | * | 6/2000 | Viebach et al. | 600/114 |

FOREIGN PATENT DOCUMENTS

| | | |
|---|---|---|
| DE | 42 42 291 A1 | 6/1994 |
| DE | PCT/EP93/03570 | 6/1994 |

* cited by examiner

*Primary Examiner*—John Mulcahy
*Assistant Examiner*—Jocelyn Ram
(74) *Attorney, Agent, or Firm*—Graybeal Jackson Haley LLP

(57) ABSTRACT

A drive mechanism for moving a shaft or rod along its central axis that utilizes a flexible eversion tube surrounding a portion of and slidingly engaged to the outer surface of the shaft or rod. The drive mechanism uses at least one wheel group having two or more drive wheels that are coplanar with each other and, along the shaft's axis of movement, are aligned with each other and spaced apart. The drive wheels are in compressive contact with a central portion of the flexible eversion tube. The at least one wheel group is supported and located around the central portion by a sleeve that surrounds the central portion of the eversion tube. The sleeve contains slits that permit the individual wheels to contact the central portion of the tube and a casing having two pivotally connected halves that when clamped together, seal the wheel groups and sleeve within its cavity and enable a drive source to drive the wheels.

19 Claims, 2 Drawing Sheets

DRIVE MEANS FOR FLEXIBLE EVERSION TUBE SYSTEM

The present invention relates to a flexible eversion tube system for an endoscopy instrument and, in particular, a drive means for the drive of a respective flexible eversion tube.

BACKGROUND OF THE INVENTION

From the prior art according to DE 42 42 291 A1, for instance, an endoscope including a flexible eversion tube design of this species is known.

This endoscope substantially comprises an endoscope head or a distal end, to which an endoscope shaft of a flexible resilient tubular body is connected, and an operating means at the rear end of the endoscope shaft. The operating means has a number of actuating wheels rotatably supported at the endoscope shaft which are operatively connected with the distal end via operating wires or Bowden cables laid inside the endoscope shaft. Furthermore a first drive or feed means exerting a driving force on the endoscope shaft via drive wheels is provided in a rear end portion of the endoscope.

Around the endoscope shaft at least in the leading portion thereof a flexible eversion tube which is driven by a second drive or feed means is arranged. The flexible eversion tube consists of an inner tube section being slidably adjacent to the surface shell of the endoscope shaft and being eversed in the area of the distal end of the endoscope to form a leading outer tube section The leading outer tube section is further returned to the second drive means and is fixed to the casing thereof. In the rear portion of the endoscope the inner tube section is eversed to form a trailing outer tube section which is likewise returned to the second drive means and is fixed to the casing thereof at the axial end face opposed to the leading outer tube section.

The second drive means acts on the inner flexible eversion tube section to move the same in the axial direction of the endoscope shaft. To this effect, the second drive means includes a kind of collar which contracts in radial direction and, in so doing, can be frictionally engaged so as to be pressed against the inner tube section and can further be moved in axial direction of the endoscope in a reciprocating manner. In another variant of this second drive means a number of friction wheels arranged at an angular distance from each other is provided, which friction wheels sit close on the inner tube section and thus exert a substantially continuous feed motion on the inner tube section. The radially acting pressing forces of the collar and/or the friction wheels of the second drive means are selected to be such that at least part of the pressing forces applied is transmitted to the surface shell of the endoscope shaft by a deformation of the material of the inner tube section so that the endoscope shaft is advanced along with the inner tube section despite the relative sliding capacity.

Since with this only type of drive by the second drive means, i.e. without the first drive means, the rate of feed of the flexible eversion tube at its leading eversing portion would only be half of that of the endoscope shaft due to the eversing movement thereof, that is to say the endoscope shaft would move out of the flexible eversion tube in a telescopic manner with an increasing penetrating depth into the hollow, the aforementioned first drive means exerts a brake force on the endoscope shaft counteracting the feed force of the second drive means.

The second drive means is synchronized with the first drive means in such manner that by interaction of the two drive means the rate of movement of the inner tube section in axial direction is approximately twice as high as the rate of movement of the endoscope shaft, the latter sliding relative to the inner endoscope shaft (i.e. the distal end of the endoscope shaft moves at the same rate as the leading eversing portion of the flexible eversion tube).

In order to facilitate the relative movement between the endoscope shaft and the flexible eversion tube, the prior art according to DE 42 42 291 A1 further provides a lubricating device by the intermediary of which a lubricant can be forced into a gap between the inner tube section and the endoscope shaft as well as into a hollow between the inner and outer tube sections. To this effect, the lubricating device, inter alia, has a tapered sleeve which is slipped on the endoscope shaft and sealingly interacts with the trailing eversing portion of the flexible eversion tube which is put on the tapered sleeve. The lubricant forced into a gap between the tapered sleeve and the endoscope shaft by a pump spreads between the inner tube section and the endoscope shaft over the total length of the flexible eversion tube, excessive quantities of the lubricant in the leading eversing portion of the flexible eversion tube penetrating into the hollow to be examined.

In accordance with an in-house prior art, the inventor is moreover involved in developing an endoscopy instrument using a double flexible eversion tube system according to the aforementioned species, as it will be briefly described hereinafter:

This endoscopy instrument comprises an endoscope shaft slidably guided in a tube eversed on both sides which in turn is movable by a drive means acting upon the inner tube section of the flexible eversion tube. The drive means comprises at least one continuous feed means, especially frictional wheels arranged at a uniform angular distance which can be pressed radially onto the inner tube section to move the latter in a substantially continuous manner in axial direction of the shaft. This has the important advantage that the continuous advance of the flexible eversion tube system can be exactly controlled and thus, for instance, the distal end of the endoscope can be guided accurately on the spot.

It is provided in this context that the pressing force of the feed means on the inner tube section is selected such that the shaft is in direct frictional contact with the inner tube section at least in the area of the feed means. The feed means is formed by one or more frictional wheels which are biased against the inner tube section at a predetermined or adjustable pressing force so that, on the one hand, a continuous feed and, on the other hand, a possibly slip-free feed of the endoscope shaft into a patient's hollow to be examined is ensured.

Moreover the drive means comprises means for synchronizing the shaft movement with the movement of the flexible eversion tube. This may be a rear or front end piece or clamping piece axially fixed to the shaft on which the trailing or leading eversing portion of the flexible eversion tube dependent on the feed direction sits close in a slidable manner so that the flexible eversion tube applies a brake force opposing the presently prevailing feed force of the feed means to the endoscope shaft via the rear or front end pieces.

Numerous tests carried out by the inventor have shown that in an endoscopy instrument of such design comprising the above-described flexible eversion tube system the feed forces applicable by the frictional wheels are limited, however. The reason herefor is that the feed forces of the frictional wheels can be applied only partially to the endoscope shaft via the inner tube section, because between the inner tube section and the surface shell of the endoscope shaft as well as between the frictional wheels and the inner flexible eversion tube section a lubricating film is formed permitting, on the one hand, a relative sliding movement between the endoscope shaft and the inner tube section and, on the other hand, causing a slip between the drive wheels and the inner tube section. This means that part of the theoretically possible feed force of the frictional wheels on the endoscope shaft gets lost. Moreover, it has turned out that the friction contacts between the individual drive wheels and the inner tube section may be different, whereby, in this case, the drive forces of the individual wheels are transmitted to the inner tube section in a nonuniform manner. The one-sided axial load of the radially inner tube section resulting herefrom entails a tilting and crinkling of the flexible eversion tube. Moreover the entire brake forces occurring to counteract the feed force of the frictional wheels depending on the direction of movement at the rear or front end piece or clamping piece of the endoscope shaft act upon the inner and outer, rear or front tube section of the flexible eversion tube, whereby an additional axial load is exerted on the same.

The above-described flexible eversion tube is made substantially of a silicone or a similar material and has such thickness which permits an as lossfree reversal as possible at the front and rear eversing portions during a movement of the endoscope shaft. However, this design only permits a relatively low axial load especially of the inner tube section along the feeding direction of the endoscope shaft by the frictional wheels and/or by the rear or front clamping piece, wherein, when a maximum admissible load limit depending on the material and the thickness thereof is exceeded, likewise a crinkling in particular of the inner tube section occurs. In this condition not only the relative sliding capacity is deteriorated, but also the maximum feed force applicable to the endoscope shaft is reduced so that the feed movement is decelerated or even stopped.

As a result of these examinations it is noted that with a flexible eversion tube design according to the foregoing description the penetrating depth of the endoscope into the hollow to be examined is limited, because with an increasing penetrating depth an increasing feed force has to be applied to the endoscope shaft, the feed force in turn being limited by the maximum loading capacity especially of the inner tube section of the flexible eversion tube.

SUMMARY OF THE INVENTION

In view of this problem, it is the object of the present invention to provide a flexible eversion tube system by which a feed force can be transmitted to an endoscope shaft, a catheter or similar shaft-like rounds in a steady and reliable manner.

This object is achieved, according to the invention, by a drive means of a flexible eversion tube system comprising the features according to claim 1.

Accordingly, the drive means for a flexible eversion tube system comprises a number of drive wheels adapted to be engaged, preferably frictionally engaged, with an inner flexible eversion tube section of a flexible eversion tube to transmit a feed force to shaft-like rounds, for instance to an endoscope shaft. According to the invention, at least two drive wheels are spaced apart from each other in driving direction, i.e. they are connected in series. Thus the entire engaging portion as well as the contacting surface between the drive wheels and the inner tube section into which the drive force (preferably a frictional force) is transmitted to the inner flexible aversion tube section is increased in axial direction of the flexible eversion tube, whereby a kind of guide is provided for the inner tube section over an axial distance. This guiding. property of the drive means is adapted to effectively prevent the radially inner flexible eversion tube section from crinkling, Moreover the series connection of drive wheels in the driving direction according to the invention has the effect that a possible slipping of any one of the drive wheels is practically harmless to the desired load transmission which is steady in circumferential direction. In other words, if any one of the drive wheels shows an increased slip due to the aforementioned lubricating film, the load transmission to the inner tube section is ensured by at least a second, axially downstream drive wheel, with the slipping wheel still being adapted to act as a guide. Thus the flexible eversion tube is likewise effectively prevented from tilting or crinkling due to a one-sided introduction of force.

It is a further effect that the pressing force of the wheels onto the flexible eversion tube may be lower because of the increased total contacting surface between the drive wheels and the inner tube section and is moreover spread onto a larger area, i.e. the surface force is reduced in total so that no deformations of the flexible eversion tube and/or the highly flexible endoscope shaft occur.

According to claim 2, it is especially advantageous to support the drive wheels in a casing which consists of at least two casing members movably hinged to each other at one side along the driving direction. In this way the flexible eversion tube -system and the drive means can be manufactured separately and mounted in a simple way.

It is moreover provided, according to claim 3, that the drive wheels form at least two drive rows spaced apart in the driving direction and each consisting of a number of, preferably four, drive wheels arranged at equal angular distance, wherein the drive wheels of all drive rows are connected to one single drive source via a common gear mechanism. Hereby not only an optimum introduction of force into the inner flexible eversion tube section is reached, but also a compact design of the gear system and thus of the entire drive means is enabled.

Further advantageous embodiments of the invention constitute the subject matter of the other subclaims.

The invention will be described hereinafter in more detail by way of a preferred embodiment with reference to the accompanying drawings.

DETAILED DESCRIPTION OF THE INVENTION

Figure 1:
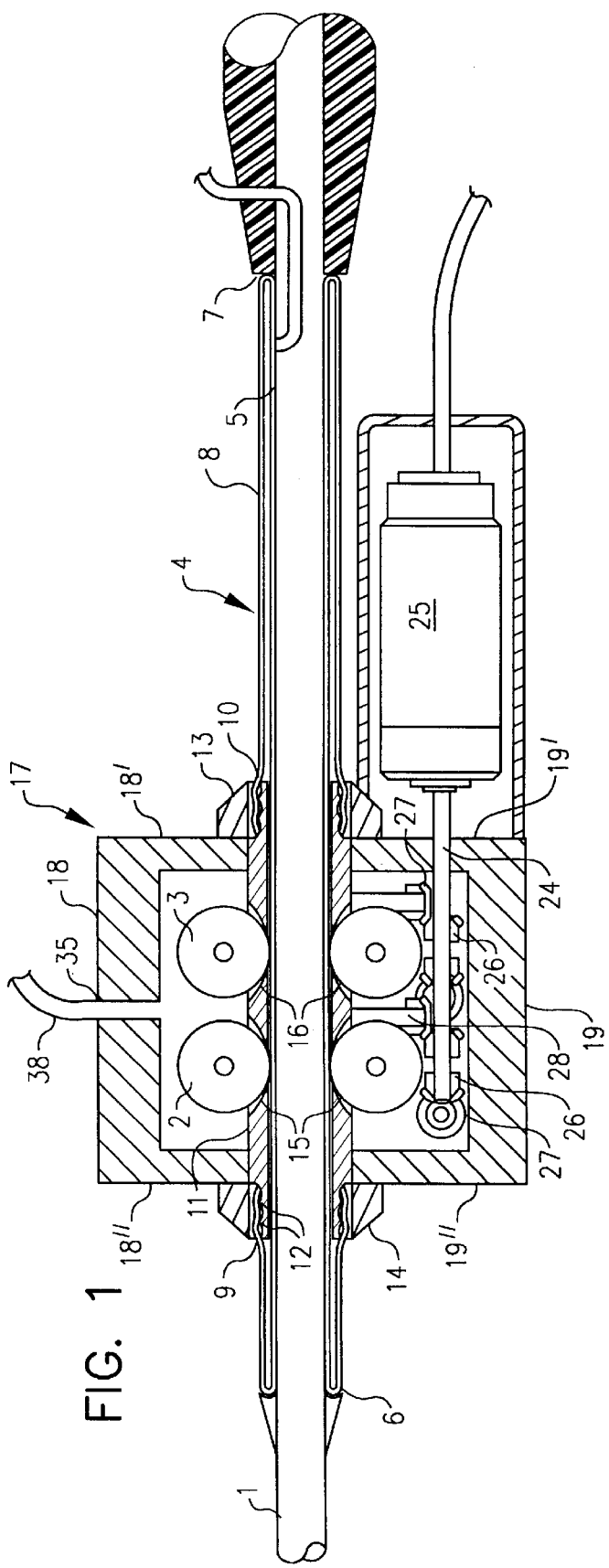
FIG. 1 shows the longitudinal section of a flexible eversion tube system including a drive means according to the preferred embodiment of the invention.

According to FIG. 1, the flexible eversion tube system comprising the drive means according to the invention is provided for feeding an endoscope shaft 1. The drive means has at least two rows of drive wheels 2, 3 arranged at an equal angular distance, wherein the at least two rows of drive wheels are spaced apart in the driving direction, i.e. along the endoscope shaft 1 to be driven.

The endoscope shaft 1 is surrounded by a flexible eversion tube 4 consisting of a radially inner tube section 5 which changes into a radially outer tube section 8 in front and rear eversing portions 6, 7. In a central portion of the flexible eversion tube 4 the radially outer tube section 8 extending from both eversing portions 6, 7 ends at both sides, whereby two opposed free tube ends 9, 10 are formed. Between these free ends 9, 10 of the flexible eversion tube 4 a sleeve 11 preferably made of synthetic material and enclosing the inner tube section 5 is arranged, on the axial end portions of which the free eversing tube ends 9, 10 of the outer tube section 8 are sealingly mounted, thereby a closed hollow space being formed between the inner and outer tube sections 5, 8.

According to FIG. 1, for this the sleeve 11 is provided with a fluting or with grooves 12 at its axially end-sided surfaces to impede a slipping of the free tube ends 9, 10 pulled onto the sleeve 11. In addition, clamping rings 13, 14 are slipped onto the sleeve ends, the free tube ends 9, 10 being pressed therebetween. The sleeve 11 furthermore includes in its central portion two axially spaced rows of recesses or slits 15, 16 which are respectively arranged at an equal angular distance. Preferably each row consists of four slits 15, 16 spaced apart from each other at an 90° angle.

As is further illustrated in FIG. 1, the drive wheels 2, 3 are accommodated in a casing 17 sealingly surrounding the sleeve 11. To this end the casing 17 is made of two casing members 18, 19 which are relatively movably hinged to each other at one side. The front and rear side walls 18', 19'; 18'', 19'' of the casing members 18, 19 include recesses 36, 37 in the form of the outer dimensions of the sleeve 11. When folding the casing members 18, 19 the sleeve 11 is thus fixedly clamped to fit exactly in the recesses 36, 37 between the casing members 18, 19, wherein seal rings 22 are additionally arranged at the opposed surfaces 20, 21 of the casing members 18, 19 to be brought into contact so as to ensure a tight seal.

The slits 15, 16 are arranged such that, when folding the casing members 18, 19, the drive wheels 2, 3 mesh with the slits 15, 16 substantially contactless and get into contact with the radially inner tube section 5. The drive wheels 2, 3 are preferably supported resiliently in the casing 17 so that the drive wheels 2, 3 are forced onto the inner flexible eversion tube section 5 or are biased, resp., in accordance with the modulus of elasticity of the elastic suspension (not shown in more detail) and thus exert a radially directed supporting force on the inner tube section 5 and are adapted to admit or compensate minor dimensioning tolerances especially with respect to the diameter of the shaft and also of the diameter of the tube, if necessary.

Figure 2:
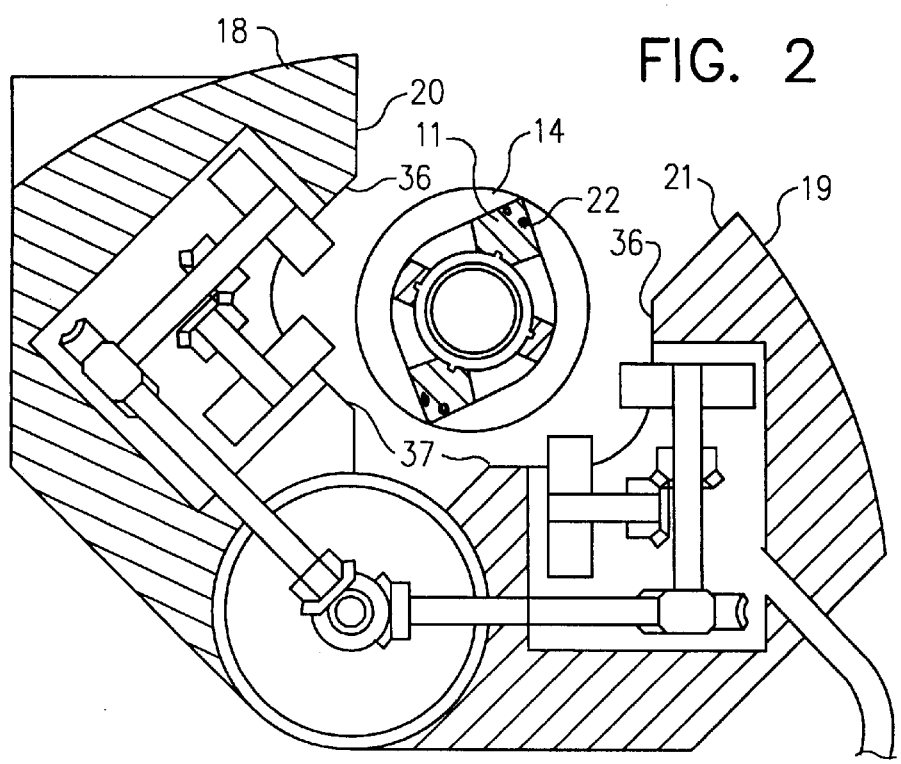
FIG. 2 shows the cross-section of the drive means in an unfolded condition of the casing without being engaged with the flexible eversion tube and FIG. 3 shows the cross-section of the drive means in an engaged condition with the flexible eversion tube for load transmission.
Figure 3:
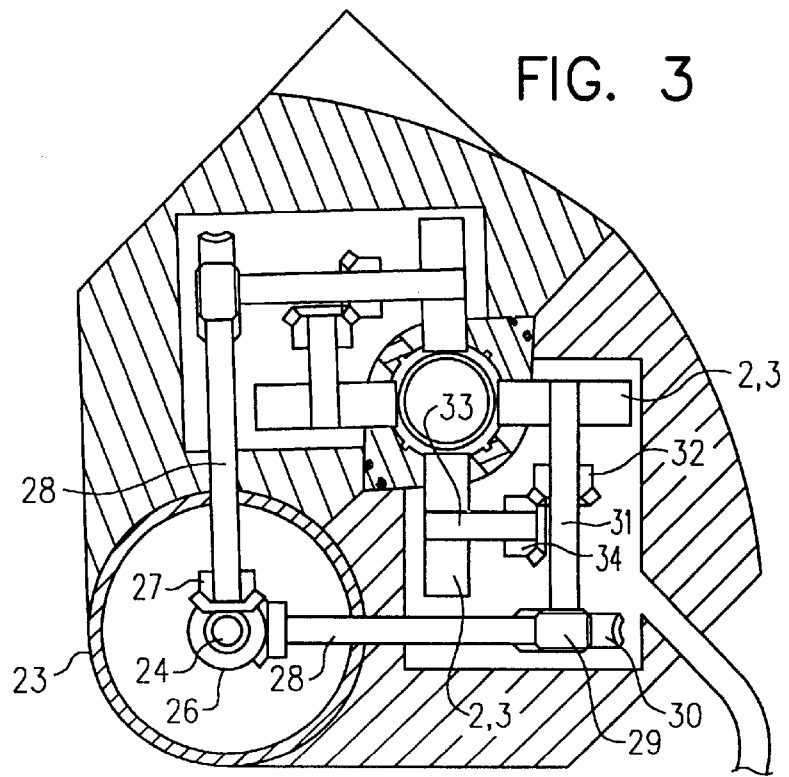

As is shown in FIGS. 2 and 3, the hinge mechanism of the casing 17 constitutes a kind of cylindrical pit or channel 23 extending along the flexible eversion tube 4, in the central axis of which channel an output shaft 24 of a drive source, preferably of an electric motor 25, is extending. Four bevel wheels 26 are fixedly mounted on this output shaft 24 at a mutual axial distance and are in mesh with bevel wheels 27 of four intermediate shafts 28. The intermediate shafts 28 are in turn operatively connected via a worm 29—worm wheel 30—gear system with a first axis of rotation 31 to each end of which a drive wheel 2, 3 is fixed. In the central portion of each first axis of rotation 31 another bevel wheel 32 is mounted so as to drive via a respective bevel wheel 34 second axes of rotation 33 to each of which likewise a drive wheel 2, 3 is fixed. Thus by this gear the driving force of the drive source, i.e. of the electric motor 25, is distributed substantially evenly to the drive wheels 2, 3 which consequently rotate at the same speed.

The casing 17 includes a fluid conduit connection 35 to which a lubricating fluid conduit 38 is connected to fill the interior of the casing with lubricant and thus to lubricate the gear system. At the same time, by the slits 15, 16 provided in the sleeve 11 the interior of the casing comprises a connection into the hollow between the outer and inner tube sections 5, 8 so that this hollow is filled with lubricant, too.

A peculiarity of the embodiment of the sleeve 11 can be best taken from FIGS. 2 and 3. Accordingly, the sleeve 11 has an eye-shaped cross-section, the casing members 18, 19 showing the corresponding recesses 36, 37 in eye shape in the area of the contact surfaces 20, 21. In the folded condition the eye-shaped sleeve 11 is thus clamped to fit exactly between the now opposed recesses 36, 37 so that their position is fixed with respect to the casing 17. In other words, the eye-shaped configuration of the sleeve 11 as well as the correspondingly shaped recesses 36, 37 of the contact surfaces 20, 21 of the casing members 18, 19 enables the sleeve 11 to be centered, thereby ensuring a uniform mesh of the drive wheels 2, 3 (uniform supporting forces) with the inner tube section 5.

What is claimed is:

1. A drive for transmitting a feed force to a shaft defining a longitudinal axis and having an outside surface, comprising:
    a flexible eversion tube having an inner tube section slidingly engaging a portion of the outside surface of the shaft; and
    at least one wheel group comprising a plurality of drive wheels, each drive wheel having a center and an axis of rotation passing through the center, each drive wheel being in compressive contact with the inner tube section, and at least one axis of rotation being substantially coplanar with and parallel to at least one other axis of rotation thereby defining a plane parallel to the longitudinal axis of the shaft.

2. A drive according to claim 1, wherein a plurality of wheel groups are equally spaced circumferentially around the longitudinal axis and operatively linked to an intermediary gear mechanism, the gear mechanism being operatively linked to a drive source.

3. A drive according to claim 2, wherein the drive source is an electric motor having an output shaft operatively coupled to the intermediary gear mechanism.

4. A drive according to claim 2, having four wheel groups circumferentially spaced 90° apart around the longitudinal axis and each wheel group having two drive wheels.

5. A drive according to claim 1, further comprising at least one second wheel group comprising one drive wheel being in compressive contact with the inner tube section of the flexible eversion tube.

6. A drive for transmitting a feed force to a shaft defining a longitudinal axis and having an outside surface, comprising:
    a flexible eversion tube having an inner tube section slidingly engaging a portion of the outside surface of the shaft;
    at least one wheel group comprising a plurality of drive wheels, each drive wheel having a center and an axis of rotation passing through the center, each drive wheel being in compressive contact with the inner tube section, and at least one axis of rotation being substantially coplanar with and parallel to at least one other axis of rotation thereby defining a plane parallel to the longitudinal axis of the shaft; and a casing enclosing and supporting the at least one wheel group with the casing having at least two casing members pivotally connected to each other along a first edge of each casing member.

7. A drive according to claim 6, wherein a plurality of wheel groups are equally spaced circumferentially around the longitudinal axis and operatively linked to an intermediary gear mechanism, the gear mechanism being operatively linked to a drive source.

8. A drive according to claim 6, wherein a drive source is mounted to one of the casing members on an exterior mounting surface.

9. A drive according to claim 6, wherein the flexible eversion tube further comprises two free tube ends and an outer tube section radially opposite the outside surface of the shaft and formed by eversing the two free tube ends over the inner tube section and toward each other.

10. A drive according to claim 9, wherein the free tube ends are sealingly fixed to a sleeve that is slipped over the inner tube section and has a plurality of slits corresponding to the number and position of the plurality of drive wheels.

11. A drive according to claim 10, wherein the sleeve further comprises an axial center portion having an eye-shaped outer contour and located between two axial end portions having a surface selected from the group consisting of a fluted surface and a surface having at least two grooves to prevent the free tube ends of the outer tube section from slipping off.

12. A drive according to claim 11, further comprising clamping rings attaching the axial end portions of the sleeve to the free tube ends thereby impeding slipping of the free tube ends off the sleeve.

13. A drive according to claim 11, wherein the casing members have contact surfaces comprising eye-shaped recesses such that the recesses mate with the eye-shaped outer contour of the axial center portion of the sleeve when the casing members are adducted, and the recesses position the slits of the sleeve to allow penetration of the wheels through the sleeve and onto the inner tube section of the flexible eversion tube.

14. A drive for transmitting a feed force to a shaft defining a longitudinal axis and having an outside surface, comprising:

a flexible eversion tube having an inner tube section slidingly engaging a portion of the outside surface of the shaft, two free tube ends, and an outer tube section radially opposite the outside surface of the shaft and formed by eversing the two free tube ends over the inner tube section and toward each other;

at least one wheel group comprising a plurality of drive wheels, each drive wheel having a center and an axis of rotation passing through the center, each drive wheel being in compressive contact with the inner tube section of the flexible eversion tube, and at least one axis of rotation being substantially coplanar with and parallel to at least one other axis of rotation thereby defining a plane parallel to the longitudinal axis of the shaft; and a sleeve having a plurality of slits corresponding to the number and position of the plurality of drive wheels, the sleeve being slipped over the inner tube section and sealingly fixed between the two free tube ends.

15. A drive according to claim 14, wherein a plurality of wheel groups are equally spaced circumferentially around the longitudinal axis and operatively linked to an intermediary gear mechanism, the gear mechanism being operatively linked to a drive source.

16. A drive according to claim 14, wherein the sleeve further comprises an axial center portion having an eye-shaped outer contour and located between two axial end portions having a surface selected from the group consisting of a fluted surface and a surface having at least two grooves to prevent the free tube ends of the outer tube section from slipping off.

17. A drive according to claim 16, further comprising clamping rings attaching the axial end portions of the sleeve to the free tube ends thereby impeding slipping of the free tube ends off the sleeve.

18. A drive according to claim 16, further comprising a casing enclosing and supporting the at least one wheel group, the casing having at least two casing members pivotally connected to each other along a first edge of each casing member, the casing members having contact surfaces comprising eye-shaped recesses wherein the recesses mate with the eye-shaped outer contour of the axial center portion of the sleeve when the casing members are adducted, and the recesses position the slits of the sleeve to allow penetration of the wheels through the sleeve and onto the inner tube section of the flexible eversion tube.

19. A drive according to claim 18, wherein a drive source is mounted to one of the casing members on an exterior mounting surface.

* * * * *